United States Patent [19]

Klok et al.

[11] Patent Number: 5,116,546
[45] Date of Patent: May 26, 1992

[54] PROCESS FOR PRODUCING FATTY-ACID LOWER-ALKYL MONO-ESTERS

[75] Inventors: Robbert Klok, Vlaardingen; Herbert H. Verveer, Ridderkerk, both of Netherlands

[73] Assignee: Van den Bergh Foods Co., Division of Conopco, Inc., Lisle, Ill.

[21] Appl. No.: 503,656

[22] Filed: Apr. 3, 1990

[30] Foreign Application Priority Data

Apr. 5, 1989 [EP] European Pat. Off. ........ 89105947.9

[51] Int. Cl.$^5$ ................................................ C11C 3/02
[52] U.S. Cl. .................................. 554/167; 554/174; 554/175; 560/234
[58] Field of Search ................... 260/410.9 R; 560/234

[56] References Cited

U.S. PATENT DOCUMENTS

| | | | |
|---|---|---|---|
| 4,303,590 | 12/1981 | Tanaka et al. | 260/410.9 |
| 4,371,470 | 2/1983 | Matsukura et al. | 260/410.9 |
| 4,608,202 | 8/1986 | Leper et al. | 560/234 |

FOREIGN PATENT DOCUMENTS

| | | | |
|---|---|---|---|
| 3020612 | 12/1980 | Fed. Rep. of Germany | 560/234 |
| 2072167 | 1/1981 | United Kingdom | 560/234 |

*Primary Examiner*—Jose G. Dees
*Assistant Examiner*—Deborah D. Carr
*Attorney, Agent, or Firm*—Gerard J. McGowan, Jr.

[57] ABSTRACT

The invention pertains to the production of high-purity fatty-acid lower-alkyl mono-esters which comprises a first transesterification step between glycerol fatty-acid esters and a lower alcohol, a separation step wherein the reaction product of the esterification step is separated into glycerol-rich and fatty-acid lower-alkyl mono-ester rich fractions, a second esterification step in which all glycerol and fatty-acid glycerolesters of the fatty-acid lower-alkyl mono-ester rich fraction are esterified to the corresponding fatty-acid triglycerolesters, and a recovery step wherein said fatty-acid lower-alkyl mono-esters are recovered.

12 Claims, No Drawings

PROCESS FOR PRODUCING FATTY-ACID LOWER-ALKYL MONO-ESTERS

The present invention relates to a process for producing fatty-acid lower-alkyl mono-esters which comprises an esterification step wherein one or more fatty-acid glycerolesters and a monohydric lower-alkylalcohol are reacted in the presence of a suitable alcoholysis catalyst to produce a mixture comprising fatty-acid lower-alkyl mono-esters, fatty-acid glycerolesters and glycerol, a separation step wherein said mixture is separated into a glycerol-rich fraction and a fraction rich in fatty-acid lower-alkyl mono-ester, and a recovery step wherein said fatty-acid lower-alkyl mono-esters are recovered from said mono-ester-rich fraction.

Processes for the production of fatty-acid lower-alkyl mono-esters using transesterification/alcoholysis reactions are well-known. In general they comprise the transesterification of, preferably at least pre-refined, oils and fats with methanol in the presence of an alkaline catalyst. After the transesterification reaction a crude glycerine layer comprising in addition to the glycerol formed in the transesterification reaction, soap formed by the catalyst, catalyst some methylesters and methanol, is separated from the fatty-acid methylester layer, which is subsequently purified by any suitable recovery method, such as e.g. distillation.

Processes of this type have been described in U.S. Pat. Nos. 2,383,596, 2,383,579, 2,383,580, 2,383,596, 2,383,599, 2,383,601, 2,383,602, 2,383,614, 2,383,632 and 2,383,633, and in the European Patent No. 0 164 643.

In the production of high-purity fatty-acid methylesters a problem is encountered in the recovery of the methylesters from the methylester-rich fraction. In particular due to the presence of fatty-acid glycerol mono-esters in the methylester fraction, high-purity separation of the fatty-acid methylesters from such glycerol esters is difficult in an economically feasible way. The separation efficiency between the methylesters and the glycerol mono-esters which can be achieved by standard distillation equipment, is such that distillation residues of in the order of 20% are necessary to avoid fatty-acid glycerol mono-esters coming over with the fatty-acid methylesters. Conventional distillation routines therefore result in unacceptably low methylester yields.

It has now been found that the problem of poor separation efficiency and the corresponding relatively low yield of high-purity fatty-acid methylester can be overcome by an extra esterification step before said recovery, but after separation of the fatty-acid methylester fraction from the glycerol fraction. In this extra esterification step the glycerol and fatty-acid glycerol mono- and di-esters present in the fatty-acid methylester fraction are reacted to the corresponding fatty-acid glycerol tri-esters. Due to the much higher separation efficiency between fatty-acid methylesters and fatty-acid glycerol tri-esters, the recovery of the high-purity fatty-acid methylesters can be conveniently achieved e.g. by conventional distilling techniques without the drawback of high distillation residues and corresponding poor yields.

Accordingly, in its broadest aspects the present invention provides a process for producing fatty-acid lower-alkyl mono-esters which comprises a first esterification step (1) wherein one or more fatty-acid glycerolesters and a monohydric lower-alkylalcohol are reacted in the presence of a suitable catalyst to produce a mixture comprising fatty-acid lower-alkyl mono-esters, fatty-acid glycerolesters and glycerol, a separation step (2) wherein said mixture produced in step (1) is separated into a glycerol-rich fraction (a) and a fraction (b) rich in fatty-acid lower-alkyl mono-ester, and a recovery step (4) wherein said fatty-acid lower-alkyl mono-esters are recovered from said fraction (b), the process further comprising a second esterification step (3) in which before said recovery step (4) substantially all glycerol and fatty-acid glycerolesters of said fraction (b) are esterified to the corresponding fatty-acid glycerol tri-esters.

The first step of the process in accordance with the invention comprises a transesterification reaction wherein a fatty mixture of one or more fatty-acid glycerolesters and a monohydric lower-alkylalcohol are reacted in the presence of an alcoholysis catalyst to produce a mixture comprising, as main components, fatty-acid lower-alkyl mono-esters and glycerol. In addition, the mixture will comprise unreacted and partially reacted fatty-acid glycerolesters, remaining catalyst, soap and lower-alkylalcohol.

As suitable fatty-acid source may be used a mixture of one or more fatty-acid glycerolesters, i.e. any mono-, di- and triglycerides of synthetic or natural origin, or mixtures thereof, comprising $C_6$–$C_{24}$, and in particular $C_{12}$–$C_{18}$ fatty-acid groups, which may be straight or branched, and saturated, or mono- or poly-unsaturated. Suitable such fatty-acid groups include laurate, myristate, palmitate, stearate, oleate, linoleate, linolenate and elaidate groups. In general a mixture of glycerides is used a substantial or full proportion whereof consists of triglyceride fats and oils obtained from vegetable or animal sources. Suitable such fats and oils include soybean oil, sunflower oil, safflower oil, rapeseed oil, peanut oil, linseed oil, shea nut oil, cottonseed oil, palm and palmkernel oils, tall oil, tallow, lard, cocoa-butter and fish oils. Such fats and oils may optionally have been partially or fully hardened, or modified by fractionation to obtain the desired fatty-acid composition.

Transesterification reactions being negatively influenced by the presence of water it is often of advantage to dry the glycerolester mixture and reduce the amount of water therein to as low a level as possible before mixing in further reactants and starting the first esterification step (1).

The monohydric lower-alkylalcohol used in the first esterification step is selected from the group of the $C_1$–$C_6$ mono-alcohols, and preferably is methanol.

The mixture of one or more fatty-acid glycerolesters and the monohydric lower-alkylalcohol are transesterified in the presence of a suitable alcoholysis catalyst. Suitable such catalysts include the group consisting of alkali metals, alkaline earth metals, and alloys thereof, as well as the alkoxides, bicarbonates, carbonates, hydrides, and hydroxides of such metals. Although in this specification all members of this group are referred to as catalysts as is done in literature, it will be understood that the alkali metal alkoxide resulting form the reaction of the above catalysts with the lower-alkylalcohol is in fact the catalyzing agent.

Accordingly, the alkali-metal alkoxide can be introduced into the reaction mixture as such or in situ prepared by addition of one of the above sufficiently strong alkaline materials to convert part of the monohydric lower-alkylalcohol to the catalyzing agent.

The first esterification reaction can be carried out using conventional transesterification/alcoholysis conditions. In general the reaction will be carried out at elevated temperature, which dependent upon the particular (blend of) fatty acid residues and alcohol involved, may range from 40° to 160° C., and in most cases will lie within the range of from 50° to 120° C., in particular of from 60° to 100° C.

It may be convenient to carry out the reaction under conditions of refluxing or alternatively in a closed reaction vessel to maintain the desired temperature and/or pressure regime. Such pressures may be atmospheric as well as sub- or super-atmospheric.

Preferably, also some agitation is applied to the reactant mixture during the first esterification reaction e.g. by way of stirring means in the reaction vessel.

In general a stoechiometric excess of the monohydric lower-alkylalcohol with respect to the fatty acid residues in the one or more fatty-acid glycerolesters is used, in particular, molar ratios of monohydric lower-alkylalcohol to glycerolester fatty-acid residues of over 1.5:1. Excess amounts corresponding to a molar ratio of between of 2:1 to 6:1 are preferred.

Relatively low amounts of catalyst can be used. Suitable such amounts lie within the range of from 0.01 to 1 mol per kg of reaction mixture. Preferred amounts of catalyst lie within the range of from 0.05 to 0.5 mol per kg of reaction mixture, amounts of from 0.1 to 0.2 mol per kg being preferred most.

Using the above described transesterification conditions, suitable reaction times range from as short as 10 minutes to several hours, reaction times in the range of 30 minutes up to 3 hours being usual.

At a sufficiently high degree of conversion to fatty-acid lower-alkyl mono-ester the reaction mixture separates into lower-layer rich in glycerol, and an upper-layer rich in the fatty-acid lower-alkyl mono-ester formed in the first esterification reaction.

Subsequent to the first esterification step the glycerol-rich layer consisting of about 60 to 75% glycerol and minor amounts of lower-alkylalcohol, mono-ester, soap and catalyzing agent can easily be withdrawn from the layer rich in fatty-acid lower-alkyl mono-ester. The glycerol-rich fraction is then worked up by conventional methods including distilling-off of the lower-alkyl alcohol optionally after adding some additional amount of catalyst to reduce the level of any remaining fatty-acid lower-alkyl mono-ester. The lower-alkyl alcohol is preferably re-used in or recirculated to the first step of the process, whereas the remainder of the glycerol-rich fraction can be fed to a conventional fat-splitting operation.

After withdrawal of the glycerol-rich fraction the remaining fraction in general comprises over 80%, and in particular over 90 or even over 95% of the fatty-acid lower-alkyl mono-ester, but also undesirable amounts of fatty-acid glycerolesters in particular of from about 1 to 5% of monoglycerides, as well as lower-alkyl alcohol, glycerol and catalyzing agent.

To obtain a mono-ester rich fraction having concentrations of glycerol and glycerides as low as possible it is of advantage to carry out the first esterification reaction such that the excess amount of monohydric lower-alkylalcohol is added to the one or more fatty-acid glycerolesters in two or more separate quantities, and to withdraw from the reaction mixture, before the addition of any further quantity of lower-alkylalcohol, the glycerol-rich layer already formed during the preceding stage of the esterification reaction. In this way the final mono-ester-rich fraction resulting after the first esterification step has a lower concentration of glycerol and glycerides.

Subsequent to the first esterification and after withdrawal of the glycerol-rich fraction, the remaining mono-ester rich fraction is submitted to esterification conditions such that all glycerol and mono-and di-glycerides present therein are caused to react with part of the fatty-acid lower-alkyl mono-esters to the corresponding tri-glycerides.

Preferably, this second 'return' esterification reaction is driven towards near completion, i.e. substantially full conversion of glycerol and glycerolesters to triglycerides, and the lower-alkyl alcohol formed during the reaction is distilled off by suitable means including conditions of elevated temperature, reduced pressure and the use of stripping agents, such as e.g. nitrogen. By substantially full conversion to triglycerides is meant that 0.5% by weight or less of partial glycerolesters remain in the resulting mixture.

Suitably, the second esterification reaction is carried out at a temperature within the range of from 70° to 120° C., preferably of from 80° to 100° C.

Often it is necessary to add a top-up amount of catalyst to the amount still remaining from the first esterification step of the process of the invention, in order to bring it to a level required for proper catalytic action in the second esterification. Suitably, at this stage of the process amounts of catalyst are added which lie within the range of from 0.01 to 0.1 mol per kg of reaction mixture. Preferably top-up amounts of catalyst are added within the range of from 0.03 to 0.06 mol per kg.

Using the above described esterification conditions, suitable reaction times range from about 1 to several hours, reaction times in the range of 1 to 3 hours being usual.

The lower-alkyl alcohol distilled off in the second esterification reaction can suitably be and preferably is re-used in or recirculated to the first step of the process.

After the second esterification reaction has been brought to substantial completion, the mono-ester rich fraction essentially consists of fatty-acid lower-alkyl mono-ester, triglyceride, soap and some catalyzing agent. The catalyst and soap components can be suitably removed by conventional water washing and filtration steps, and used as a feed-stock for soap production.

In the final step of the process of the invention the mixture of fatty-acid lower-alkyl mono-ester and tri-glyceride is submitted to a distillation step in which owing to the improved separability resulting after the second esterification step in accordance with the present invention the fatty-acid lower-alkyl mono-esters are separated off in high purity to a distillation residue of less than 10%, preferably less than 8% or even less than 6%.

The distillation residue consists of a mixture of substantially all the triglycerides and a remaining part of the fatty-acid lower-alkyl mono-ester, and suitably can and preferably is recirculated to the reaction mixture in the first esterification step of the process of the invention.

The process of the invention is particularly directed to the production of fatty-acid lower-alkyl mono-esters of high purity, in particular food-grade purity. By the process of the invention purities can be achieved of over 99%, or even over 99.8%.

The process of the invention allows the production of high-purity fatty-acid lower-alkyl-alkyl mono-esters without excessive poor yields in the final distillation step. It further allows an economically feasible use of all side-product streams produced in the process either to yield valuable feedstocks and/or raw materials or to be recirculated into feedstocks used in the process of the present invention.

The process of the present invention will now be further illustrated by way of the preferred embodiments described in the following examples.

EXAMPLE 1

A mixture of 40 kg of refined and dried soybean oil and 6.2 kg methanol was heated to 65° C. under refluxing conditions. To this mixture 0.95 kg of a 30 wt.% solution of sodium methoxide in methanol was added. After 1.5 hours reaction time the mixture was allowed to settle for about 1 hour. After settling the resulting two layers were separated yielding 4.9 kg of a glycerol-rich fraction and about 41.3 kg of a fraction rich in fatty-acid methylester.

Subsequently, a further 0.2 kg of a 30 wt.% solution of sodium methoxide in methanol was added to the methylester fraction, and the methanol was distilled off under vacuum while raising the temperature slowly to 80° C. (about 3 hours). To remove the methanol substantially completely nitrogen stripping was applied.

The mixture was then washed with about 3.5 l of demineralised water at 40° C. Subsequently, the lower layer (water-soap emulsion) was separated off, about 38 kg of a clear methylester layer remaining. The methylester fraction was stirred for 5 minutes with 1% of a conventional bleaching earth (Tonsil standard FF ®) and then filtered. After filtration (taking about 4 hours) 35.7 kg of methylester fraction was obtained.

The methylester fraction was subsequently distilled to a residue of 5.7% yielding a soybean fatty-acid methylester having an OH-value of 0.8 and an acid-value of 0.07.

EXAMPLE 2

On a technical scale a mixture of 1100 kg of refined and dried soybean oil and 170 kg methanol was heated to 65° C. in a closed reaction vessel (1.3 bar). To this mixture 26 kg of a 30 wt.% solution of sodium methoxide in methanol was added. After 1.5 hours reaction time the mixture was allowed to settle for about 1 hour. After settling the resulting two layers were separated yielding 150 kg of a glycerol-rich fraction and about 1140 kg of a fraction rich in fatty-acid methylester.

Subsequently, a further 5 kg of a 30 wt.% solution of sodium methoxide in methanol was added to the methylester fraction, and the methanol was distilled off under vacuum while raising the temperature slowly to 80° C. (about 1.5 hours). To remove the methanol substantially completely nitrogen stripping was applied.

The mixture was then washed with about 190 l of water at 40° C. Subsequently, the lower layer (water-soap emulsion) was separated off, about 1125 kg of a clear methylester layer remaining. The methylester fraction was stirred for 5 minutes with 10 kg of a conventional bleaching earth (Tonsil standard FF ®) and then filtered. After filtration (taking about 3 hours) 1110 kg of methylester fraction was obtained.

The methylester fraction was subsequently distilled to a residue of 4.5% yielding a soybean fatty-acid methylester having an acid-value of 0.07 and a monoglyceride level of about 0.4 wt.%.

We claim:

1. In a process for producing fatty-acid lower-alkyl mono-esters which comprises a first esterification-step (1) wherein one or more fatty-acid glycerolesters and a monohydric lower-alkylalcohol are reacted in the presence of an alcoholysis catalyst to produce a mixture comprising fatty-acid lower-alkyl mono-esters, fatty-acid glycerolesters and glycerol, a separation step (2) wherein said mixture produced in step (1) is separated into a glycerol-rich fraction (a) and a fraction (b) rich in fatty-acid lower-alkyl mono-ester, and a recovery step (4) wherein said fatty-acid lower-alkyl mono-esters are recovered from said fraction (b), the improvement comprising a second esterification step (3) in which before said recovery step (4) substantially all glycerol and fatty-acid glycerolesters of said fraction (b) are esterified to the corresponding fatty-acid glycerol tri-esters.

2. The process of claim 1 in which the monohydric lower-alkylalcohol is selected from the from the group of the $C_1$–$C_5$ mono-alcohols.

3. The process of claim 2 in which the monohydric lower-alkylalcohol is methanol.

4. The process of claim 1 in which during the second esterification step (3) lower-alkylalcohol is removed by distillation.

5. The process of claim 1 in which the second esterification step (3) is carried out at a temperature within the range of from 70° to 120° C.

6. The process of claim 1 in which in the second esterification step (3) a top-up amount of catalyst is introduced into fraction (b).

7. The process of claim 6 in which the top-up amount of catalyst is within the range of from 0.01 to 0.1 mol per kg of fraction (b).

8. The process of claim 1 in which the second esterification step (3) is continued to a level of partial glycerolesters in fraction (b) of 0.5% by weight or less.

9. The process of claim 4 in which the lower-alkyl alcohol removed by distillation in the second esterification step (3) is recirculated to the reaction mixture of the first esterification step (1).

10. The process of claim 1 in which in the recovery step (4) the fatty-acid lower-alkyl mono-esters are distilled to a distillation residue of less than 10%.

11. The process of claim 10 in which said distillation residue is less than 6%.

12. The process of claim 10 in which said distillation residue is recirculated to the reaction mixture of the first esterification step (1).

* * * * *